United States Patent [19]

Takubo

[11] Patent Number: 4,657,592
[45] Date of Patent: Apr. 14, 1987

[54] ROOT CANAL SEALER

[75] Inventor: Masayoshi Takubo, No. 19-1, Osasa 3-chome, Chuo-ku, Fukuoka-shi, Fukuoka-ken, Japan

[73] Assignees: Masayoshi Takubo; Michihiro Takubo, both of Fukuoka, Japan

[21] Appl. No.: 782,216

[22] Filed: Sep. 30, 1985

[30] Foreign Application Priority Data

Oct. 4, 1984 [JP] Japan ................... 59-208698

[51] Int. Cl.$^4$ ................................. C09K 3/00
[52] U.S. Cl. ................................. 106/35; 106/272
[58] Field of Search ............... 106/35, 272; 433/217

[56] References Cited

U.S. PATENT DOCUMENTS 4,129,134 12/1978 Hind et al. ..................... 131/2

Primary Examiner—Lorenzo B. Hayes
Attorney, Agent, or Firm—Bucknam and Archer

[57] ABSTRACT

A root canal sealer containing medium chain fatty acid triglyceride instead of eugenol, the sealer further contains calcium hydroxide or calcium oxide and bees wax, the blending ratio of the medium chain fatty acid triglyceride and bees wax is 5:95–30:70 by weight, the sealer being applied to an apical foramen together with gutta percha cone using ultra sonic technology, the sealer enables to employ the calcium ingredient in a desired ratio and the solidifying of the sealer may be accelerated.

4 Claims, No Drawings

ROOT CANAL SEALER

BACKGROUND OF THE INVENTION

Among the dental diseases caused by dental caries, there are pulpitis and infected root canal. In case of a healthy tooth, a central cavity (root canal) runs in the longitudinal direction within the tooth, and the root canal opens a fine hole (apical foramen) at the tip of the tooth, which receives blood through this fine hole, and nourishes the nerve fiber (dental pulp). When affected by pulpitis, the patient, suffering from a great deal of pain, will visit a dentist. In case of an infected root canal with developed necrosis of the pulp, on the other hand, lesion may sometimes develop within the tissue surrounding the root apex (periapical tissue). In such cases, previous treatment often consisted extracting the diseased tooth. With the progress of dental techniques, however, the operative dentistry to preserve the tooth (diseased tooth) without extracting it has become more popular. At present the practice is to remove the inflamed dental pulp under local anasthesia (extirpation of the pulp), or in case of an infected root canal, to remove the infected dentin, then clean, disinfect and fill the hollowed root canal compact with a filling material (canal filling). Variations depending on the dentist will make the kind of the tooth (such as canine, molar tooth or the like), the size of the tooth that varies according to the age and sex of the patient, the individual dietetics (this is considerably variant), and the conditions and the stage of the diseased tooth, and will give the treatment to the interior of the root canal (endodontic therapy), and preserve the diseased tooth.

Hereinafter, the filling agent to be used in canal filling in the endodontic therapy will be explained somewhat in detail. The surfaces of the root canal after extirpation of the pulp and the infected root canal are not only smooth but have the remaining protein, and particularly in case of the infected root canal, there are various impurities such as microorganisms and pus, and the surface of the root canal itself, being infected by microorganisms, is softened (soft dentin) to form a lesion deeply infected by microorganisms. The operation to disinfect chemically the interior of the root canal, is carried out then the infected dentine is removed using a reamer, and at the same time, the shape of the root canal (preparation of root canal). The basic technique of the preparation of the root canal is to enlarge the root canal with a reamer, then scrape the wall with a needle-like file similar in shape with that of a reamer, (the kind of file being able to scrape the surface when drawn inward) to smooth the wall surface. The disinfection and preparation of the root canal are the operating techniques that require a high technique and a good deal of patience but are quite important to carry out successfully the canal filling that follows and to preserve the diseased tooth in a favorable condition. The root canal itself is curved in many cases, and varies being branched (collateral routes) or narrowed in the middle, and has an anatomical shape so complicated that there are no root canals alike. In the interior of the prepared root canal, filling is compactly placed. The condition of the canal filling, whether it has been done well or not, becomes a factor that exerts a good deal of influence over the therapeutical process subsequent thereto. There are various filling materials that are called root canal sealers and the technique of filling also vary. But there are requirements for the root canal sealer; that is it can be completely solidified within the root canal after filling, and the components of the root canal sealer do not disintegrate out from the apical foramen, and of course it can be easily handled by the operator in filling.

CONVENTIONAL ROOT CANAL SEALERS

Root canal sealers are closely related with the technique of root canal filling and are classified in the following three types (a), (b) and (c).

(a) Root canal sealers that solidify in root canal: The root canal sealers are in a pasty state before it is applied into the root canal, and solidify at the temperature of the body); the typical sealer is zinc oxide-eugenol cement. As an appropriate example of the local products, there is "Canals ®" (a product of Showa Yakuhin Kako Co., Ltd.) in Japan. This root canal sealer is a mixture consisting of zinc oxide, rosin, bismuth subcarbonate and barium sulfate as the essential ingredients in the ratio of blend 40:30:15:15, in the form of white powder. The accelerator is a mixture consisting of eugenol (clove oil) and olive oil in the ratio of blend 83:17, in the form of pale yellow liquid. In application, these two agents, each in an optimal portion, are mixed by the operator to form a stringent paste, and when filled in the root canal, zinc oxide and eugenol are reacted and solidified within about 30 minutes so that the interior of the root canal can be compactly filled. The use of the cement for filling the root canal is the standard of the endodontic therapy, and there are either the cases where the cement itself is used alone, and where it is used as the assistant material in the canal filling by use of a gutta percha cone (which is to be explained later), later. The latter method is considered the proper procedure. As the canal cement that solidifies in the root canal, there are the products in a flexible tube convenient for mixing, and in addition, there are cements where no eugenol is used.

(b) Root canal sealers which are solidify within the root canal:

This type of products is quite convenient for the operator because they needn't be mixed, but since they do not solidify in the root canal, they cannot be said permanent root canal sealer. But since diseased teeth are to be shed in the future, this type of root canal sealers is useful for desiduous tooth. When a germicide is added in the product, it is useful as a paste for disinfection treatment within the root canal, but it must be removed from the root canal after disinfection is completed.

(c) Root canal sealers that contain calcium hydroxide or calcium oxide:

Calcium hydroxide or calcium oxide is a remedy that promotes the healing mechanism of the root apex through calcification (cement formation), and categorically they medicines. As for the calcium hydroxide preparations for dental use commercially available and used at present, the method of root canal filling where the preparation is first applied so as to spread sufficiently throughout the root apex, and after the excess and unnecessary preparation is removed, mechanical filling is performed by using the other canal filling cement and a gutta percha cone (which is to be explained later) has been disclosed.

In application of the aforementioned root canal sealer to the root canal, a gutta percha cone for canal filling is used. The gutta percha cone for canal filling is a needle of natural resin of the length about 30 mm, having a shape tapered off at the point, fit to the shape of the root canal, and the thickness is standardized. It is made from natural gutta percha resin with beeswax, Japan wax, barium sulfate and zinc white, and is called as "gutta percha cone". Though it is standardized, a space is left between the gutta percha cone and the wall of the root canal when it is actually applied, therefore, the cone is inserted with a root canal cement previously applied in combination. In many cases, conventionally, the root canal cement used for the purpose has ben "Canals ®."

The reason of the combination use of the gutta percha cone and the root canal cement is to press in the cement into the collateral route which cannot be filled with the gutta percha cone.

In filling the root canal according to the conventional technique, the cement is first kneaded to a desired consistency, which is then applied to the gutta percha cone and inserted in the root canal, then a hand spreader (a fine gimlet curved in L-shape) is inserted into the root canal to press the cone against the canal wall to form a space, and into said space a fine size cone (a secondary cone) is inserted in the same position occupied by the spreader. By the repetition of this operation, the interior of the root canal is filled with gutta percha cone, and the cement serves for filling the space left thereby.

The above operation is the basis of the conventional art and its outline, and based thereon we explain hereinafter its complicatedness, difficulties and defects.

The cement for canal filling in the conventional art is mixed with such powder as zinc white and (or) a contrast medium and a liquid such as a setting agent, etc. to a thick and stringent consistency, it is difficult to spread it thoroughly within the fine root canal, and it requires a high technique to spread it through the collateral route. The cement of prior art has another inconvenience that when it is subjected to heat, setting is accelerated so that it may happen that setting starts during the operation. On the other hand, gutta percha cone is softened when warmed, and it has a characteristic that at the body temperature, it becomes a hard rubber-like solid. Accordingly, there has been a need of a rood canal sealer having a desirable characteristics such that even when it is warmed within a root canal, it does not exert any influence over the setting reaction, and rather when warmed, the root canal sealer is melted and becomes homogeneous with the gutta percha cone.

The cement of the conventional art has to be mixed each time when it is used, and therefor it is inconvenient in operation. When a spreader is inserted, the cement and the gutta percha cone are not melted together, so that they cannot be integrated within the root canal, being left separate as they are, and as a result there may be the fear of leaving a dead space. In such a dead space, the tissue fluid would be stored in the future, and would be infected. On the other hand, when the cement is extruded from the apical foramen, the patient may sometimes complain of a light ill feeling for several days caused by local irritation of eugenol. Not a few studies have been made conventionally to prevent the extrusion of the cement and form a calcareous layer rapidly at the root apex (it has been considered an ideal healing biologically that the apical foramen is closed by the formation of the calcareous layer). The preparation of root canal has been intended to prevent the extrusion, and more careful canal-filling operations have been done. For and for the formation of the calcareous layer, there are the test results of the cases where calcium hydroxide (or calcium oxide) was used. To use calcium hydroxide (or calcium oxide), it would be convenient if a calcium hydroxide preparation could be used in combination with the canal filling eugenol cement of the conventional art. However, since the calcium hydroxide (or calcium oxide) reacts with eugenol and accelerates the setting of the cement, the use of calcium hydroxide (or calcium oxide) in combination with eugenol is quite difficult.

DESCRIPTION OF THE INVENTION

The present invention relates to a root canal sealer to be used in application of root canal filling to a tooth by using a gutta percha cone and ultrasonic technology.

The inventor of the present invention has accomplished the present invention after his researches for a composition of root canal sealer that could simplify the complicated operation of the conventional art, improve the incompatibility of the ingredients, and to improve procedure that allows to blend calcium hydroxide (or calcium oxide) previously therewith so as that dentists could cope with various conditions of the diseased teeth by mere application of the basic operation, and that even relatively inexperienced doctors could treat them with high efficiency.

The shapes of apical foramens vary, but the question will arise when the apical foramen is wider than the root canal; in such a case the root canal sealer may extrude from the root apex even under a careful operation by an experienced doctor. Once it extrudes through the apical foramen, it causes physical harm to the periapical tissue. One reason is due to the chemical components of the root canal sealer, and another is that the setting of the root canal sealer in the root canal physically presses the periapical tissue. For these reasons it is a basic idea not to allow extrusion of the root canal sealer from the apical foramen, but there may be also cases in which the extrusion cannot be avoided as we have mentioned before. Even in case of the root canal sealer of the present invention, extrusion may sometimes occur, and when the apical foramen is wider than the root canal, extrusion may not be avoided as in the case of the conventional art. The inventor of the present invention, however, studied and developed a novel idea and technique to use the root canal sealer of the present invention for the preparation of root canal. Utilizing the characteristic of the sealer of the present invention when part A alone is extruded but part B is not, it causes no harmful physiological reaction in the periapical tissue. Since the part A of the present invention, on the other hand, has little physiological reaction chemically and retains a semi-solid state in a living body, it does not exhibit such harmful action to press physically the periapical tissue, and leads to an ideal healing by the deposition of calcareous layer in the apical foramen as it is absorbed in the living body.

Further examined the composition of root canal sealer of the present invention has the characteristics that when warmed within a root canal, it can be readily melt-mixed with the gutta percha, and at a body temperature it retains a semi-solid state. The inventor has discovered that the above requirements may be fulfilled only when a medium chain triglyceride (hereinafter referred to as MCT) is blended with the root canal sealer composition.

MCT can be produced by using fatty acids having equal carbon number through semi-synthesis or distillation. Compared with natural vegetable oils, its carbon number is low, and therefore it has a low viscosity, and as it is not a natural product, its quality is definite and it has a high purity. Said MCT is now used widely as a vehicle of non-aqueous intramuscular injections, and has proved to be free from cytotoxicity, has little tissue-irritant characteristic, and good absorbability.

Any product so called MCT can be usable in the present invention, but for the time being, the medium chain triglyceride (Trade Marks: Miglyol ® 812, Miglyol 810, Miglyol 818), the products of Dynamit Nobel, West Germany (handled by Mitsuba Trading Co., Ltd.) can be used successfully because of its tint, viscosity, purity, and co-solvency with the gutta percha cone. The carbon number of the medium chain triglyceride is $C_8$-$C_{12}$.

To the medium chain triglyceride, barium and (or) bismuth compounds are added in addition to zinc oxide to obtain a root canal sealer. Because, the hard tissue called tooth itself has a radiopaque characteristic, and it is impossible to confirm the contrast between the tooth and the root canal sealer on a film unless a compound having a relatively strong radiopaque characteristic is used for the root canal sealer that exists in the center of the tooth. Accordingly, the root canal sealer needs to be blended with a large amount of such insoluble-inorganic compound as barium and (or) bismuth. And in order to make it possible to mix a large amount of the insoluble-inorganic powder together with a small amount of oil, as small as possible, MCT, an oil of low viscosity (of low molecular weight), was selected in the present invention.

In the method where the root canal sealer of the present invention is used, it is impossible to dissolve the gutta percha cone within the root canal if the amount of MCT is too small. Accordingly, the lower limit of the amount of MCT can be set up by confirming dissolution of said cone. The upper limit, on the other hand, can be limited depending on the blending amounts of eucalyptol, thymol, rosin, etc.

In restricting a suitable amount of use of MCT in the root canal sealer of the present invention, it was confirmed to be suitable to limit the blending ratio between MCT and bees wax to the range of 5:95-30:70. The preferable blending ratio is about 10:90. Hereinafter we explain the ground of our restricting the blending ratio to the above range.

The inventor of the present invention carried out an experiment on the minimum, or the most suitable amount of use of MCT by using root canal models (10×10×30 mm) made of a transparent methyl methacrylate resin. This model may be considered as the tooth of methylmethacrylate in which a fine hole is perforated as a root canal, which has been widely used for the practices and researches of root canal filling. For simplification, the test was carried out by using MTC+bees wax, and five samples were blended changing the blending ratio of the two components as 2:98, 5:95, 10:90, 20:80, 30:70. Each sample was heated and melted, and thoroughly agitated, and when the sample was cooled to 40° C., a gutta percha cone was inserted in the melt-mixture then immediately withdrawn to be solidified, so that the surfaces of each gutta percha cone were covered with said melt-mixture. The gutta percha cones thus obtained were inserted one by one in the models of root canal, then according to the method of the present invention, the softening and melting conditions of the cones were observed on every side of the exterior, using an ultrasonic tip. All the five samples were softened by the tip, but differences were noted in the process and the time of melting; in case of the sample having the blending ratio 2:98, it was hardly softened, and in case of the sample of the blending ratio 5:95, melting took a long time. The samples of the blending ratio more than 10:90, were softened within a short time, and within the root canals, formation of a melt-mixture of MCT, bees wax and the gutta percha was observed. As a result, the most suitable blending ratio was found to be about 10:90.

The root canal sealer of the present invention is composed of part A containing calcium hydroxide or calcium oxide and part B containing neither calcium hydroxide nor calcium oxide. Said part A contains calcium hydroxide or calcium oxide and closes the apical foramen by accelerating calcification at the root apex; thus it is, so to speak, a biological root canal sealer, which retains itself a semi-solid state within a living body. Part B, on the other hand, is a root canal sealer which is applied to the root canal section including the collateral route, together with part A, and melting the gutta percha point and sealing physically the interior of the root canal and accelerates as the result the solidifying action. As we have mentioned hereinabove, the present invention has succeeded to blend calcim hydroxide or calcium oxide in a desired blending ratio by using MCT, i.e. medium chain triglyceride, instead of eugenol that was conventionally used; and it has made it possible to simplify the complicated operation of root canal filling and has enabled even an inexperienced doctor to practice root canal filling by using the root canal sealer of the present invention with a high rate of success.

We hereinafter explain concrete Examples of the invention.

EXAMPLE 1

Part A is composed of powders and liquids (refer to Table 1) and the operator can use them by blending each suitable amount of them into a pasty state at the time of use. But it is also possible to mix 2 parts of the powder with 1 part of the liquid to form a paste, which is then divided into flexible tubes or small injection syringes as the standard part A and place them on the market.

TABLE 1

| Composition of Part A | | |
|---|---|---|
| Component | % by weight | % by weight [Mixture of powder + liquid (2:1)] |
| Powder | | |
| Calcium hydroxide[1] | 30 | 20 |
| Barium sulfate[1] | 25 | 17 |
| Bismuth subcarbonate | 25 | 17 |
| Zinc oxide[1] | 15 | 10 |
| Allantoin | 5 | 3 |
| Liquid | | |
| Beeswax[1] | 10 | 3 |
| MCT | 60 | 20 |
| Rosin[1] | 4 | 1 |
| Thymol[1] | 26 | 9 |
| | | Total 100 |

[1]Pharmacopoeial grade

Part B is likewise composed of powders and liquids (refer to Table 2) and the operator can use them by mixing to give a paste, or use them by mixing 3 parts of the powder with 1 part of liquid to form a paste as standard part B.

TABLE 2

Composition of Part B

| Component | % by weight | % by weight [Mixture of powder + liquid (3:1)] |
|---|---|---|
| Powder | | |
| Zinc oxide[1] | 40 | 30 |
| Rosin[1] | 30 | 22 |
| Bismuth subcarbonate | 15 | 11 |
| Barium sulfate[1] | 15 | 11 |
| Liquid | | |
| Eucalyptol[1] | 18 | 5 |
| MCT | 17 | 4 |
| Gutta percha | 35 | 9 |
| Thymol[1] | 30 | 8 |
| | | Total 100 |

[1]Pharmacopoeial grade

As was set forth in the foregoing, both part A and part B were composed of powders and liquids, which is an arrangement so that the blending ratio between part A and part B could be adjusted by the operator to mix them into a root canal sealer of a desired consistency at the time of use. However, it would be more convenient for the operator in handling and in operation if the powders could previously be prepared into a pasty state.

The composition (root canal sealer) of the present invention can be placed on the market, as a standard part A and as standard part B in such forms as a combination of powder and liquid, or as separate ointments, or a paste prepared by mixing them previously, being separately divided in a flexible tube or a small injection syringe as part A or part B so as to be immediately used as they are, or in the form of part A or part B alone.

The method of use is quite simple. Part A in a pasty state is filled in an injection syringe (an injection syringe for tuberculin having a long body is suitable), to which a needle is fixed that is cut off at the tip and edgeless and at the point about 30 mm from the tip bent at an angle about 100°. The ultrasonic spreader is preferable to be of suitable shape as well as the materials. It was named "ultrasonic root canal tip," or "tip" in brief. Therefore it is referred to hereinafter as the "tip". Into the prepared root canal, part A was first placed by using the aforementioned injection syringe, then the tip as we described above was inserted and oscillated. As ultrasonic oscillation and heat generation took place within the root canal, the fluidity of part A was increased and it penetrated into canaliculus dentalis and collateral route.

In the next step, a gutta percha cone coated with part B was mixed into a pasty state, then it was inserted into root canal. When the ultrasonic oscillator was set to work and the tip was inserted into the canal, part A and part B were melted together, and the gutta percha cone was also melted therein. By the insertion of the tip, the gutta percha was softened and it was melt-mixed with part A and part B. Subsequently the cone was condensed against the canal wall by using the hand spreader of the conventional art, and a fine size cone was inserted into the same position occupied by the spreader. The operation was repeated several times. In this way, calcium hydroxide was placed in the apical foramen and the melt mixture of the root canal sealer of the present invention and the gutta percha cone was placed compact within the root canal while maintaining its fluidity. At the same time by the application of the oscillation of the tip, all the collateral route and the dents in the canal wall were completely filled, and at the body temperature these were solidified as they were: thus the root canal treatment was perfectly completed.

We hereinafter show the compositions of said part A and part B in Examples 2-5. The operation with the use thereof is equal with what was practiced in Example 1.

EXAMPLE 2

Part A

| Component | % by weight | % by weight [Mixture of powder + liquid (2:1)] |
|---|---|---|
| Powder | | |
| Calcium hydroxide[1] | 35 | 23 |
| Bismuth subcarbonate | 25 | 17 |
| Zinc oxide[1] | 40 | 26 |
| Liquid | | |
| Bees wax[1] | 20 | 7 |
| MCT | 55 | 18 |
| Rosin[1] | 5 | 2 |
| Eucalyptol[1] | 20 | 7 |
| | | Total 100 |

Part B

| Component | % by weight | % by weight [Mixture of powder + liquid (4:1)] |
|---|---|---|
| Powder | | |
| Zinc oxide[1] | 35 | 28 |
| Bismuth subcarbonate | 25 | 20 |
| Rosin[1] | 35 | 28 |
| Calcium phosphate[1] | 5 | 4 |
| Liquid | | |
| MCT | 50 | 10 |
| Eucalyptol | 50 | 10 |
| | | Total 100 |

[1]Pharmacopoeial grade

EXAMPLE 3

Part A

| Component | % by weight | % by weight [Mixture of powder + liquid (2:1)] |
|---|---|---|
| Ointment (a) | | |
| Calcium hydroxide | 30 | 20 |
| Barium sulfate | 40 | 27 |
| MCT | 25 | 17 |
| Aluminum monostearate | 5 | 3 |
| Ointment (b) | | |
| Bees wax | 30 | 10 |
| Eucalyptol | 20 | 6.5 |
| Rosin | 30 | 10 |
| MCT | 17 | 5.5 |
| Aluminum monostearate | 3 | 1 |
| | | Total 100 |

Part B

| Component | % by weight | % by weight |
|---|---|---|
| Ointment (a) | | |
| Zinc oxide | 40 | 27 |
| Bismuth subcarbonate | 30 | 20 |
| MCT | 30 | 20 |

-continued

Part B

| Component | % by weight | % by weight |
|---|---|---|
| Ointment (b) | | |
| MCT | 50 | 16 |
| Eucalyptol | 35 | 12 |
| Colloidal silica | 10 | 3 |
| Bees wax | 5 | 2 |
| | | Total 100 |

[1] Pharmacopoeial grade

EXAMPLE 4

Part A

| Component | % by weight | % by weight [Mixture of powder + liquid (2:1)] |
|---|---|---|
| Powder | | |
| Calcium hydroxide | 30 | 20.0 |
| Zinc oxide | 40 | 26.5 |
| Bismuth subcarbonate | 20 | 13.3 |
| Rosin | 10 | 7.0 |
| Liquid | | |
| MCT | 50 | 16.6 |
| Rosin | 30 | 10.0 |
| Thymol | 10 | 3.3 |
| Vaseline | 10 | 3.3 |
| | | Total 100.0 |

Part B

| Component | % by weight | % by weight [Mixture of powder + liquid (2:1)] |
|---|---|---|
| Powder | | |
| Zinc oxide | 35 | 23.3 |
| Rosin | 35 | 23.3 |
| Bismuth subcarbonate | 30 | 20.0 |
| Liquid | | |
| Eucalyptol | 15 | 5.0 |
| MCT | 25 | 8.0 |
| Gutta Percha | 40 | 13.4 |
| Japan wax or Bees wax | 20 | 7.0 |
| | | Total 100.0 |

[1] Pharmacopoeial grade

EXAMPLE 5

Part A

| Component | % by weight | % by weight |
|---|---|---|
| Powder | | |
| Calcium hydroxide[1] | 30 | 20 |
| Barium sulfate[1] | 25 | 17 |
| Bismuth subcarbonate | 25 | 17 |
| Zinc oxide[1] | 15 | 10 |
| Allantoin | 5 | 3 |
| Liquid | | |
| Bees wax[1] | 15 | 4.5 |
| MCT | 65 | 22.0 |
| Rosin[1] | 4 | 1.0 |
| Thymol[1] | 16 | 5.5 |
| | | Total 100.0 |

[1] Pharmacopoeial grade

As for part B in this example, the part B used in Example 4 is suitable.

I claim:

1. In the root canal filling wherein a root canal sealer is used with a gutta percha cone and a heating device, and wherein the root canal sealer contains calcium hydroxide or calcium oxide and beeswax together with zinc oxide and an accelerator, the improvement comprising, as the accelerator, a medium chain fatty acid triglyceride and the blending ratio between said medium chain fatty acid triglyceride and beeswax is 5:95–30:70 by weight.

2. The root canal sealer according to claim 1 consisting of part A and part B, part A containing calcium hydroxide or calcium oxide and part B containing the remainder of ingredients and free of said calcium compound, at least one of said parts containing the medium chain fatty acid triglyceride and beeswax.

3. The root canal sealer according to claim 2, wherein said medium chain fatty acid triglyceride contains 8–12 carbon atoms and each of said part A and part B is an ointment or a paste.

4. The root canal sealer according to claim 2, wherein said part A consists of a powder containing 30–35 parts by weight of calcium hydroxide and a liquid containing 10–20 parts of beeswax and 50–65 parts of said medium chain fatty acid triglyceride and said part B consists of a powder containing zinc oxide and a liquid, containing 50–17 parts of said medium chain fatty acid triglyceride.

* * * * *